United States Patent [19]

Brownewell

[11] 4,348,480

[45] Sep. 7, 1982

[54] PROCESS FOR PRODUCING GLUCOSE ISOMERASE

[75] Inventor: Charles E. Brownewell, Elkhart, Ind.

[73] Assignee: Miles Laboratories, Inc., Elkhart, Ind.

[21] Appl. No.: 156,496

[22] Filed: Jun. 4, 1980

[51] Int. Cl.³ ............................................... C12N 9/92
[52] U.S. Cl. ..................................... 435/234; 435/94; 435/836
[58] Field of Search .......................... 435/234, 94, 836

[56] References Cited

U.S. PATENT DOCUMENTS

| | | | |
|---|---|---|---|
| 3,826,714 | 7/1974 | Suekane et al. | 435/234 X |
| 3,956,066 | 5/1976 | Coker et al. | 435/234 X |
| 3,979,261 | 9/1976 | Outtrup | 435/234 |
| 4,061,539 | 12/1977 | Lee | 435/234 X |
| 4,255,521 | 3/1981 | Hirohara et al. | 435/234 |
| 4,283,496 | 8/1981 | Lee | 435/253 |

*Primary Examiner*—Lionel M. Shapiro
*Attorney, Agent, or Firm*—Louis E. Davidson

[57] ABSTRACT

A novel glucose isomerase enzyme useful for the conversion of glucose to fructose can be prepared by growing under aerobic conditions a culture of *Bacillus licheniformis* ATCC 31604 in a medium containing appropriate nutrients and then recovering the enyzme therefrom.

1 Claim, No Drawings

PROCESS FOR PRODUCING GLUCOSE ISOMERASE

BACKGROUND AND DISCUSSION OF PRIOR ART

Sweet syrups are widely used in the baking, confectionery and beverage industries, for example. These syrups generally consist of sucrose (cane sugar) or dextrose-containing products obtained from starch hydrolysis as the principal sweetening agent. When a syrup is needed that is sweeter than that obtained from sucrose, an invert sugar syrup is employed. This is produced by acid hydrolysis of sucrose to produce a mixture of about 50 percent glucose (dextrose) and about 50 percent fructose (levulose). While glucose is somewhat less sweet than sucrose, the fructose is considerably sweeter than sucrose so that the overall sweetness is increased as compared to sucrose.

It is well known that dextrose can be converted under alkaline conditions to fructose. This conversion has great potential value in the production of sweet syrups. However, the alkaline conversion has not been commercially successful because the alkaline reaction produces an undesirably high ash level in the product syrup which is uneconomical to remove. The syrup is not acceptable unless this ash is removed. Alkaline isomerization and its attendent problems are discussed in U.S. Pat. No. 3,383,245.

The prior art then turned to an enzyme conversion of glucose to fructose. It was found that species of *Pseudomonas hydrophila, Streptomyces flavovirens, Streptomyces achromogenus, Streptomyces echinatur, Streptomyces albus, Streptomyces olivaceus,* and *Bacillus coagulans,* for example, could be grown in appropriate nutrient media to form enzymes having glucose isomerase properties. This is described in U.S. Pat. Nos. 2,950,228; 3,616,221; 3,625,828; and 3,979,261, for example. None of the known prior art suggests the use of a *Bacillus licheniformis* species to produce a glucose isomerase having the desirable characteristics of being stable under a wide range of pH and temperature conditions.

SUMMARY OF THE INVENTION

In accordance with the present invention, a process is provided for the production of a glucose isomerase comprising growing under aerobic conditions a culture of *Bacillus licheniformis* ATCC 31604 in a medium containing appropriate nutrients and then recovering the enzyme therefrom. The invention also includes a novel enzyme produced by the above process.

DESCRIPTION OF THE INVENTION

The organism useful in the present invention was isolated from a soil sample and is classified as *Bacillus licheniformis* according to well-known procedures. The particular strain of *Bacillus licheniformis* useful in the production of the novel glucose isomerase has been deposited with the American Type Culture Collection, Rockville, Md. and has been given the identification number ATCC 31604. This culture is available to the public without restriction.

The *Bacillus licheniformis* ATCC 31604 organism is maintained on agar slants and can be grown in a medium containing appropriate nutrients. The medium preferably contains xylose, corn steep liquor and a source of nitrogen. Preferably the medium also contains appropriate salts. Illustrative nitrogen sources are yeast extract, peptone, meat extract, amino acids and the like. Illustrative inorganic salts are ammonium sulfate, dipotassium phosphate, magnesium sulfate, manganese sulfate and the like. The xylose employed in the growth medium can be in a purified form or it can be in the form of a crude xylose-containing material.

The organism preferably is grown under submerged fermentation conditions for about 18 to 20 hours at a temperature of from about 50° C. to about 60° C. At temperatures below about 50° C. the yield of enzyme becomes quite low, while at temperatures above about 60° C. the growth of the organism is poor with attendant low enzyme activity. The preferred growth temperature is from about 50° C. to about 55° C. Atmospheric pressure conditions are preferably employed, but pressures above and below atmospheric can be used if desired with no particular advantages or disadvantages. The pH of the growth medium should be maintained in the range from about 6 to about 8.2. At pH conditions below about 6 and above about 8.2 there is no enzyme produced. The preferred pH is from about 6.5 to about 7.5.

The glucose isomerase of the present invention is formed inside the bacterial cells which grow during its production. The cells can be separated from the fermentation beer by well-known means, such as filtration or centrifugation, and used directly as a source of glucose isomerase. Such cells can be agglomerated and the enzyme activity immobilized therein by well-known techniques, such as the glutaraldehyde treatment disclosed in U.S. Pat. No. 3,779,869. Alternatively, the cells could be ruptured either mechanically or by autolysis and the soluble enzyme separated from the cell debris. The soluble enzyme can be used directly or it can be immobilized on a suitable carrier by well-known techniques.

The invention will be described in further detail in the following examples.

EXAMPLE I

A culture of *Bacillus licheniformis* ATCC 31604 was streaked over a solid medium of an aqueous mixture containing 3.0 percent agar-agar, 8.0 percent corn steep liquor, 0.4 percent xylose, 0.5 percent yeast extract, 0.5 percent $(NH_4)_2SO_4$, 0.1 percent $K_2HPO_4$, 0.02 percent $MgSO_4.7H_2O$, 0.005 percent $MnSO_4.H_2O$ and adjusted to pH 7.0 with sodium hydroxide. All the above percents were on a weight/volume basis. The inoculated medium was incubated at 55°–60° C. for 20 hours. The resulting cells were then scraped from the surface of the medium and were suspended in 0.9 weight percent aqueous sodium chloride to form a rather heavy cell suspension.

One ml of an aqueous solution containing 8.0 percent glucose, 0.5 percent $MgSO_4.7H_2O$, 0.05 percent $CoCl_2.6H_2O$ and 0.0001 M tris (hydroxymethyl) aminomethane was placed in a suitable container. The percents were on a weight/volume basis. To this was also added 0.2 ml. chloroform. The pH of the mixture was adjusted to 6.5 with hydrochloric acid. To this was then added 1 ml. of the above suspension and the resulting mixture was incubated at 70° C. for four hours. One drop of the product mixture was placed on Whatman No. 1 Chromatographic Paper. A drop of 0.5 weight percent aqueous fructose solution was also placed on the paper. After the two spots were dried, each spot was contacted with a portion of a color developing solution consisting of a mixture of 250 mg. naphthalenediol, 250 ml. ethanol and 20 ml. concentrated hydrochloric acid. The two treated spots were then dried for 30 min. at 25° C. and were then heated at 60° C. for up to 20 min. A similar brown-red color resulted in each spot. This indicated that the glucose isomerase enzyme activity in the cell suspension converted some of the above glucose solution to a fructose solution containing at least 0.5 weight percent fructose. It also demonstrates the production of a glucose isomerase that is active at the elevated temperature of 70° C.

EXAMPLE II

Portions of a culture of *Bacillus licheniformis* ATCC 31604 were each transferred to nine 250 ml. baffled flasks each containing 100 ml. of an aqueous mixture containing 1 percent xylose, 8.0 percent corn steep liquor, 0.5 percent yeast extract, 0.5 percent $(NH_4)_2SO_4$, 0.1 percent $K_2HPO_4$, 0.02 percent $MgSO_4.7H_2O$ and 0.005 percent $MnSO_4.4H_2O$. The percent values were on a weight/volume basis. The pH was 6.8–7.0 after sterilization. The cultures were added in an amount of 2 volume percent. These flasks were then incubated at 50° C. for 20 hours on a rotary shaker table rotating at 300 RPM. The contents of the nine flasks were then pooled to form a uniform inoculum.

Portions of the above-prepared inoculum were added to two agitated aerated fermentors each containing 10 liters of the aqueous medium described above. The inoculum was added in an amount of 2.25 volume percent to each fermentor. The agitator was rotated at 500 RPM and air was passed through the medium at a rate of 0.75 volumes of air per volume of medium per minute. An antifoam agent was added as required to minimize foam formation. The pH was maintained at 7.0 by addition of 50 weight percent aqueous xylose solution whenever the pH began to rise above 7.0. The fermentation was continued at 50° C. for 20 hours. The contents of both fermentors were then combined. A 6.1 liter portion of the combined fermentation beer was then centrifuged to separate the cells. The cells were then slurried in deionized water to a total volume of 700 ml.

To a 230 ml. portion of the above slurry were added with stirring 5.8 ml. of 10 weight percent aqueous glutaraldehyde solution. The resulting mixture was then allowed to stand without mixing for 1 hour at ambient temperature (25° C.). The slurry appeared to increase in viscosity after standing. The resulting slurry was then diluted with 460 ml. of deionized water while stirring. While continuing to stir, 30 ml. of 5 percent (weight/volume basis) aqueous polyethylenimine solution was slowly added. During this addition, a very heavy floc formed. The resulting cell mass was collected by filtration and the filter cake was washed with about 200 ml. of deionized water. The washed cake was dried overnight at 60° C. A total of 22.2 gm. of dried material was obtained. The resulting material was then milled and sieved to obtain fractions that (1) passed through a 20 mesh screen but were retained on a 30 mesh screen and that (2) passed through a 30 mesh screen but were retained on a 40 mesh screen. These mesh sizes are in the U.S. screen series. A mixture of 5 gm of the above fraction (1) and 3.6 gm. of the above fraction (2) was placed in a suitable container and hydrated for four hours with 100 ml. of a 30 weight percent aqueous mixture of 95 DE corn syrup containing 4.1 mM $MgSO_4.7H_2O$ and 4.1 mM $NaHSO_3$ adjusted to pH 8.5. The hydrated slurry was then transferred to a 1.5×100 cm. glass jacketed column having a 5 ml bed of alumina as a base support for the enzyme particles. The column was then filled with the above corn syrup substrate mixture and the contents were heated to 65° C. by means of a circulating water bath. The exit tube from the column was connected to a polystaltic pump to control the substrate flow through the enzyme bed. The top of the column was connected to a substrate reservoir. The substrate flow through the column was adjusted so as to maintain a constant 42 weight percent fructose content in the liquid leaving the column. The column contents were maintained at pH 8.0. It took about 29 days of continuous operation for the enzyme particles to decay to 50 percent of the initial activity and 37 days to decay to 25 percent of the initial activity. This demonstrates the long useful life of the *Bacillus licheniformis* glucose isomerase at 65° C.

EXAMPLE III

Ten 1 ml. portions of the *Bacillus licheniformis* ATCC 31604 slurried cells prepared as in Example II above were individually placed into 16×125 mm. screw cap tubes. The pH of the contents of the various tubes were individually adjusted to specific values between 6.5 and 8.5. Five of the tubes were held at ambient room temperature (about 25° C.) for one hour. The other five tubes were held at 70° C. for one hour. During this time the samples were not in contact with a glucose solution or any stabilizing metal ions.

The contents of each of the tubes were then assayed for glucose isomerase activity according to the following procedure. To each tube were added 0.5 ml. of an aqueous solution containing 1 M glucose, 0.1 M Hepes buffer (pH 7.0), 0.02 M $MgSO_4.7H_2O$ and 5 mM $MaHSO_3$. The tubes were then incubated at 70° C. for 30 min. The reaction was then terminated by the addition of 10 ml. of 1 M $HClO_4$. The tubes were then centrifuged. A 0.05 ml. portion of the supernatant liquid from each tube was then mixed with 1 ml. of 0.5 weight percent aqueous cysteine hydrochloride and 4.5 ml. of 75 weight percent aqueous $H_2SO_4$. The mixture was incubated for 30 min. at 35° C. and then allowed to stand for 15 min. at ambient room temperature. The absorbance of the resulting yellow colored solution at a wavelength of 412 nm. was then measured and compared with corresponding absorbance values of solutions containing known quantities of fructose to determine the fructose content of the sample. Glucose isomerase activity is expressed in units wherein the units equal the micromoles of fructose formed per minute under the conditions of the assay. The specific sample assayed as above having the highest glucose isomerase activity was then arbitrarily designated as the benchmark against which the other samples were compared. The results are shown in the following table.

TABLE

| | Relative Whole Cell Activity | |
|---|---|---|
| pH | Room Temperature | Heated at 70° C. |
| 6.5 | 73.9 | 70.1 |
| 7.0 | 87.0 | 83.6 |
| 7.5 | 97.0 | 88.9 |
| 8.0 | 92.6 | 93.5 |
| 8.5 | 100. | 97.5 |

It can be seen from the above data that the glucose isomerase produced by *Bacillus licheniformis* ATCC 31604 is generally not seriously affected by pH conditions in the range of 6.5 to 8.5 nor by elevated temperature (70° C.) in the absence of stabilizing glucose or metal ions.

What is claimed is:

1. A process for the production of a glucose isomerase comprising growing under aerobic conditions a culture of *Bacillus licheniformis* ATCC 31604 in a medium containing appropriate nutrients and then recovering the enzyme therefrom.

* * * * *